(12) United States Patent
Franci et al.

(10) Patent No.: US 10,662,125 B2
(45) Date of Patent: *May 26, 2020

(54) PET TRACER PURIFICATION SYSTEM

(71) Applicant: GE Healthcare Limited, Buckinghamshire (GB)

(72) Inventors: Xavier Franci, Loncin (BE); Steve Lignon, Loncin (BE); Audrey Marie Lange, Loncin (BE); Nicolas Verbrugge, Loncin (BE)

(73) Assignee: GE HEATLHCARE LIMITED, Buckinghamshire (GB)

( * ) Notice: Subject to any disclaimer, the term of this patent is extended or adjusted under 35 U.S.C. 154(b) by 276 days.

This patent is subject to a terminal disclaimer.

(21) Appl. No.: 15/526,245

(22) PCT Filed: Nov. 12, 2015

(86) PCT No.: PCT/EP2015/076481
§ 371 (c)(1),
(2) Date: May 11, 2017

(87) PCT Pub. No.: WO2016/075261
PCT Pub. Date: May 19, 2016

(65) Prior Publication Data
US 2017/0313632 A1 Nov. 2, 2017

(30) Foreign Application Priority Data
Nov. 12, 2014 (GB) .................. 1420093.5

(51) Int. Cl.
*C07B 59/00* (2006.01)
*B01D 15/18* (2006.01)
(Continued)

(52) U.S. Cl.
CPC ........ *C07B 59/005* (2013.01); *B01D 15/1871* (2013.01); *B01D 15/322* (2013.01);
(Continued)

(58) Field of Classification Search
CPC ............ B01J 2219/00927; B01J 19/004; B01J 19/08; B01J 19/081; C07B 59/00; C07B 59/002; C07B 59/005; C07B 2200/05
See application file for complete search history.

(56) References Cited

U.S. PATENT DOCUMENTS 10,220,105 B2 * 3/2019 Wynn ................ A61K 51/0455
2011/0305618 A1 * 12/2011 Graham ................ A61K 51/04
423/249

(Continued)

FOREIGN PATENT DOCUMENTS

JP    2010270068 A    12/2010
KR   20140097225 A    8/2014
(Continued)

OTHER PUBLICATIONS

International Search Report from International Appl. No. PCT/EP2015/076481, dated Jan. 26, 2016.
(Continued)

*Primary Examiner* — Jill A Warden
*Assistant Examiner* — Dwayne K Handy
(74) *Attorney, Agent, or Firm* — Arent Fox, LLP

(57) ABSTRACT

The present invention provides a new chemical process, a new cassette configuration, and new software for the automated production of multiple batches of an [$^{18}$F]-labelled compound on a single cassette. The invention allows one synthesizer in one hot cell to produce sequentially a plurality of batches of [$^{18}$F]-labelled PET tracer in the same day. In particular, the present invention provides a novel arrange-
(Continued)

ment useful for purifying two consecutive batches of a reaction mixture comprising an $^{18}$F-labelled compound.

15 Claims, 5 Drawing Sheets

(51) Int. Cl.
*B01D 15/32* (2006.01)
*B01D 15/36* (2006.01)
*C07H 5/02* (2006.01)

(52) U.S. Cl.
CPC ......... *B01D 15/325* (2013.01); *B01D 15/363* (2013.01); *C07B 59/00* (2013.01); *C07H 5/02* (2013.01); *C07B 2200/05* (2013.01)

(56) References Cited

U.S. PATENT DOCUMENTS

| | | | | |
|---|---|---|---|---|
| 2012/0108858 | A1* | 5/2012 | Kiselev | A61K 51/0491 570/123 |
| 2012/0283490 | A1* | 11/2012 | Gangadharmath | B01J 4/008 570/153 |
| 2017/0106104 | A1* | 4/2017 | Wynn | B01D 15/325 |

FOREIGN PATENT DOCUMENTS

| | | |
|---|---|---|
| WO | 2011/044406 A2 | 4/2011 |
| WO | 2012/083094 A1 | 6/2012 |
| WO | 2013/049608 A | 4/2013 |
| WO | 2013079578 A1 | 6/2013 |
| WO | 2013/144052 A1 | 10/2013 |
| WO | 2015/071288 A1 | 5/2015 |

OTHER PUBLICATIONS

Written Opinion of the International Searching Authority from International Appl. No. PCT/EP2015/076481, dated Jan. 26, 2016.
Great Britain Search Report from GB Appl. No. GB1420093.5, dated Sep. 1, 2015.
Korea Notice of Preliminary Rejection corresponding to Korean Application No. 10-2017-7012364, dated Dec. 6, 2019 (with English translation).
Japan Notice of Reasons for Rejection corresponding to Japanese Application No. 2017522903, dated Dec. 27, 2019 (with English translation).

* cited by examiner

PET TRACER PURIFICATION SYSTEM

TECHNICAL FIELD OF THE INVENTION

The present invention concerns devices and methods for the automated synthesis of [$^{18}$F]-labelled compounds, in particular those suitable for use as in vivo imaging agents for positron emission tomography (PET). The focus of the present invention is for the automated synthesis of more than one batch of an [$^{18}$F]-labelled compound using just one disposable cassette and in particular a novel system for purification of an [$^{18}$F]-labelled compound following the labelling reaction.

DESCRIPTION OF RELATED ART

Radiolabelled compounds for use as in vivo imaging agents are currently typically prepared by means of an automated synthesis apparatus (alternatively "radiosynthesizer"). Such automated synthesis apparatuses are commercially available from a range of suppliers, including: GE Healthcare; CTI Inc.; Ion Beam Applications S. A. (Chemin du Cyclotron 3, B-1348 Louvain-La-Neuve, Belgium); Raytest (Germany) and Bioscan (USA). The radiochemistry takes place in a "cassette" or "cartridge" designed to fit removably and interchangeably onto the apparatus, in such a way that mechanical movement of moving parts of the apparatus controls the operation of the cassette. Suitable cassettes may be provided as a kit of parts that is assembled onto the apparatus in a number of steps, or may be provided as a single piece that is attached in a single step, thereby reducing the risk of human error. The single piece arrangement is generally a disposable single use cassette which comprises all the reagents, reaction vessels and apparatus necessary to carry out the preparation of a given batch of radiopharmaceutical.

The commercially-available GE Healthcare FASTlab™ cassette is an example of a disposable single piece type of cassette pre-loaded with reagents comprising a linear array of valves, each linked to a port where reagents or vials can be attached. Each valve has a male-female joint which interfaces with a corresponding moving arm of the automated synthesis apparatus. External rotation of the arm thus controls the opening or closing of the valve when the cassette is attached to the apparatus. Additional moving parts of the apparatus are designed to clip onto syringe plunger tips, and thus raise or depress syringe barrels. The FASTlab™ cassette has 25 identical 3-way valves in a linear array, examples of which are shown in FIGS. 1 and 2. FIG. 1 is a schematic drawing of the commercially-available FDG Phosphate FASTlab™ cassette, and FIG. 2 the commercially-available FDG Citrate FASTlab™ cassette.

Synthesis of [$^{18}$F]fluorodeoxyglucose ([$^{18}$F]FDG) on the cassettes of FIGS. 1 and 2 is carried out by nucleophilic fluorination using [$^{18}$F]fluoride produced by a $^{18}$O(p,n)$^{18}$F$^-$ reaction. The $^{18}$F$^-$ so-produced enters the cassette at position 6 (i.e. 6$^{th}$ valve from the left) and travels to a QMA (quaternary methyl ammonium anion exchange) solid phase extraction (SPE) column placed at position 4 via tubing at position 5. The $^{18}$F$^-$ is retained by an ion-exchange reaction and the $^{18}$O-water is allowed to flow through the common pathway of the cassette to be recovered at position 1. $^{18}$F$^-$ retained on the QMA is then eluted with an eluent solution (acetonitrile solution of Kryptofix™ 222 and potassium carbonate at position 2, marked "Eluent") withdrawn in the syringe at position 3 and into the reaction vessel (illustrated to the bottom of the figure and connected by three tubings, one leading to each of positions 7, 8 and 25). Water is evaporated and mannose triflate precursor (from position 12, marked "Precursor") is added to the reaction vessel. Then the $^{18}$F-labelled mannose triflate ($^{18}$F-fluoro-tetraacetyl-glucose, FTAG) is trapped and so separated from $^{18}$F fluorides on an environmental tC18 SPE column at position 18 via tubing at position 17 to undergo hydrolysis with NaOH (from the vial at position 14, marked "NaOH")) to remove acetyl protecting groups. The resulting hydrolyzed basic solution is then neutralized in the syringe placed at position 24 with phosphoric acid in the case of phosphate configuration (FIG. 1) or hydrochloric acid present in a citrate buffer in the case of citrate configuration (FIG. 2). Potential residual $^{18}$F fluoride removal takes place on an alumina SPE column at position 20 via tubing at position 21 and removal of weakly hydrophilic impurities on an HLB SPE column (for the phosphate cassette of FIG. 1) or a tC18 SPE column (for the citrate cassette of FIG. 2) at position 22 via tubing at position 23. The final purified solution of $^{18}$F-FDG is transferred to a collection vial via long tubing connected at position 19.

2 positions on the FASTlab™ cassette are free in the case of each of the known [$^{18}$F]FDG cassettes illustrated in FIGS. 1 and 2, i.e. positions 9 and 10. Caps are placed on the valves at these positions.

A typical [$^{18}$F]FDG production site produces a minimum of 2 batches of [$^{18}$F]FDG a day. However, because of the residual activity on the FASTlab™ cassette, transfer line and the shadow from the waste bottle after completion of a batch, it is impossible for safety reasons to carry out back to back runs of the above-described process on the same apparatus. Furthermore, it is only possible to fit one FASTlab™ apparatus in a hot cell. To produce a second batch of [$^{18}$F]FDG on the same day using this process, it is necessary to have a second apparatus in a second hot cell.

It would therefore be desirable to have a means to produce more than one batch of [$^{18}$F]FDG using the FASTlab™ on the same day and in only one hot cell. For both of the above-described commercially-available FASTlab™ [$^{18}$F] FDG cassettes, 23 of the total 25 positions are used. With only 2 positions to spare, it is not possible to fit all the duplicate components for a second batch onto the same cassette.

WO2015071288 describes a FASTlab™ cassette for the synthesis of two batches of [$^{18}$F]FDG. FIG. 3 illustrates this cassette and although quite good yields are reported for each [$^{18}$F]FDG batch and there is quite good trapping and elution of the incoming activity, the present inventors have found problems with this configuration. First of all, contamination of the manifold with enriched water is possible because of the pathway taken for enriched water recovery to the right of the manifold for the second batch. This presents a risk for the second labelling reaction. Also, as a consequence of using up seven positions for the QMA arrangement there are limited options for placement of the other components. In particular, the Oasis HLB purification column is directly connected to the alumina column so that there is no way to properly clean the Oasis HLB after the first batch because of the risk of contaminating the alumina column with organic solvent. As a result, there is a risk that non-negligible amounts of Kryptofix 2.2.2 will be present in the final product from the second batch.

It would therefore be desirable to have an improved arrangement of the FASTlab™ cassette for carrying out two [$^{18}$F]FDG runs.

SUMMARY OF THE INVENTION

In one aspect the present invention provides a system (1) for purifying two consecutive batches of a reaction mixture comprising an $^{18}$F-labelled compound wherein said system comprises:
  (i) a reversed-phase solid phase extraction (SPE) column (2) having a first end (2a) and a second end (2b), wherein each of said first end (2a) and said second end (2b) is selectively fluidly connected to a common pathway (3); and,
  (ii) first (4) and second (5) normal-phase SPE columns, each having a first end (4a, 5a) selectively fluidly connected to said common pathway (3) and a second end (4b, 5b) fluidly connected to a product collection vial (6, 7).

In another aspect the present invention provides a single-use cassette (11) for preparing two consecutive batches of an [$^{18}$F]-labelled compound wherein said cassette comprises:
  (a) a reversed-phase SPE column (12) having a first end (12a) and a second end (12b), wherein each of said first end (12a) and said second end (12b) is selectively fluidly connected to a common pathway (13), and means (12c) for cleaning said SPE column; and,
  (b) first (14) and second (15) normal-phase SPE columns, each having a first end (14a, 15a) selectively fluidly connected to said common pathway (13) and a second end (14b, 15b) fluidly connected to a product collection vial (16, 17).
  (c) two anion exchange SPE columns (18, 19);
  (d) a reaction vessel (20a) and means (20b) for cleaning said reaction vessel;
  (e) a vial (21) containing sufficient eluent for said two consecutive batches;
  (f) a vial (22) containing sufficient precursor compound for said two consecutive batches;
  (g) reagent vials (23, 24, 25, 26) each containing a particular reagent in sufficient quantity for said two consecutive batches;
  (h) a SPE column (27a) for deprotection and means (27b) for cleaning said SPE column.

In a further aspect the present invention provides a method for purifying a first batch and a second batch of a reaction mixture comprising an $^{18}$F-labelled compound wherein said method comprises:
  (I) passing said first batch of said reaction mixture through a reversed-phase SPE column (2);
  (II) eluting said reversed-phase SPE column (2) to obtain a partially purified first batch of said reaction mixture;
  (III) passing said partially purified first batch of said reaction mixture through a first normal-phase SPE column (4);
  (IV) eluting said first normal-phase SPE column (4) to obtain a purified first batch of said reaction mixture;
  (V) passing said purified first batch of said reaction mixture into a product collection vial;
  (VI) cleaning said reversed-phase SPE column (2); and,
  (VII) passing said second batch of said reaction mixture through said cleaned reversed-phase SPE column (2);
  (VIII) eluting said reversed-phase SPE column (2) to obtain a partially purified second batch of said reaction mixture;
  (IX) passing said partially purified second batch of said reaction mixture through a second normal-phase SPE column (5);
  (X) eluting said second normal-phase SPE column (5) to obtain a purified second batch of said reaction mixture;
  (XI) passing said purified second batch of said reaction mixture into a product collection vial.

In a yet further aspect the present invention provides a method for the production of a first batch and a second batch of an $^{18}$F-labelled compound wherein said method comprises:
  (A) labelling a first aliquot of a precursor compound with $^{18}$F-fluoride;
  (B) optionally deprotecting the $^{18}$F-labelled product of step (A) on a reversed-phase SPE column;
  (C) carrying out steps I-VI of the method for purifying a first batch and a second batch of a reaction mixture comprising an $^{18}$F-labelled compound as defined herein on the reaction mixture comprising an $^{18}$F-labelled compound obtained from steps (A) and (B);
  (D) cleaning the reversed-phase SPE column(s);
  (E) labelling a second aliquot of a precursor compound with $^{18}$F-fluoride; (F) optionally deprotecting the $^{18}$F-labelled product of step (D) on a reversed-phase SPE column;
  (G) carrying out steps VII-XI of the method for purifying a first batch and a second batch of a reaction mixture comprising an $^{18}$F-labelled compound as defined herein on the reaction mixture comprising an $^{18}$F-labelled compound obtained from steps (E) and (F).

In another aspect the present invention provides a non-transitory storage medium comprising computer readable program code, wherein execution of the computer readable program code causes a processor to carry out the steps of the method of the invention as defined hereinabove.

The present invention permits good yields for the production of two batches of [$^{18}$F]-labelled compound. With the system of the present invention ethanol can be used in the conditioning of SPE columns, in the cleaning steps between first and second batches, and can be used as a radiostabilizer if desired. The reversed-phase column used for purification in the system of the present invention can be rinsed between runs with ethanol and water independently of the alumina column such that there is a negligible amount of Kryptofix™ 222 in the both batches of [$^{18}$F] labelled compound, thereby providing an advantage over WO2015071288 where the second batch has a higher concentration.

Furthermore, as described in Example 2, there was no release of extractables from the alumina column due to the fact that the alumina columns are not washed with water before use with the exemplary system of the present invention. There was therefore no impact on the quality of the product obtained from both batches and two consecutive batches of [$^{18}$F]-FDG having similar chemical and radiochemical profiles were obtained from one single-use cassette of the invention. This is important for [$^{18}$F]-FDG and other [$^{18}$F]-labelled PET tracers where defined pharmacopoeial parameters need to be met.

DETAILED DESCRIPTION OF THE PREFERRED EMBODIMENTS

Figure 1:
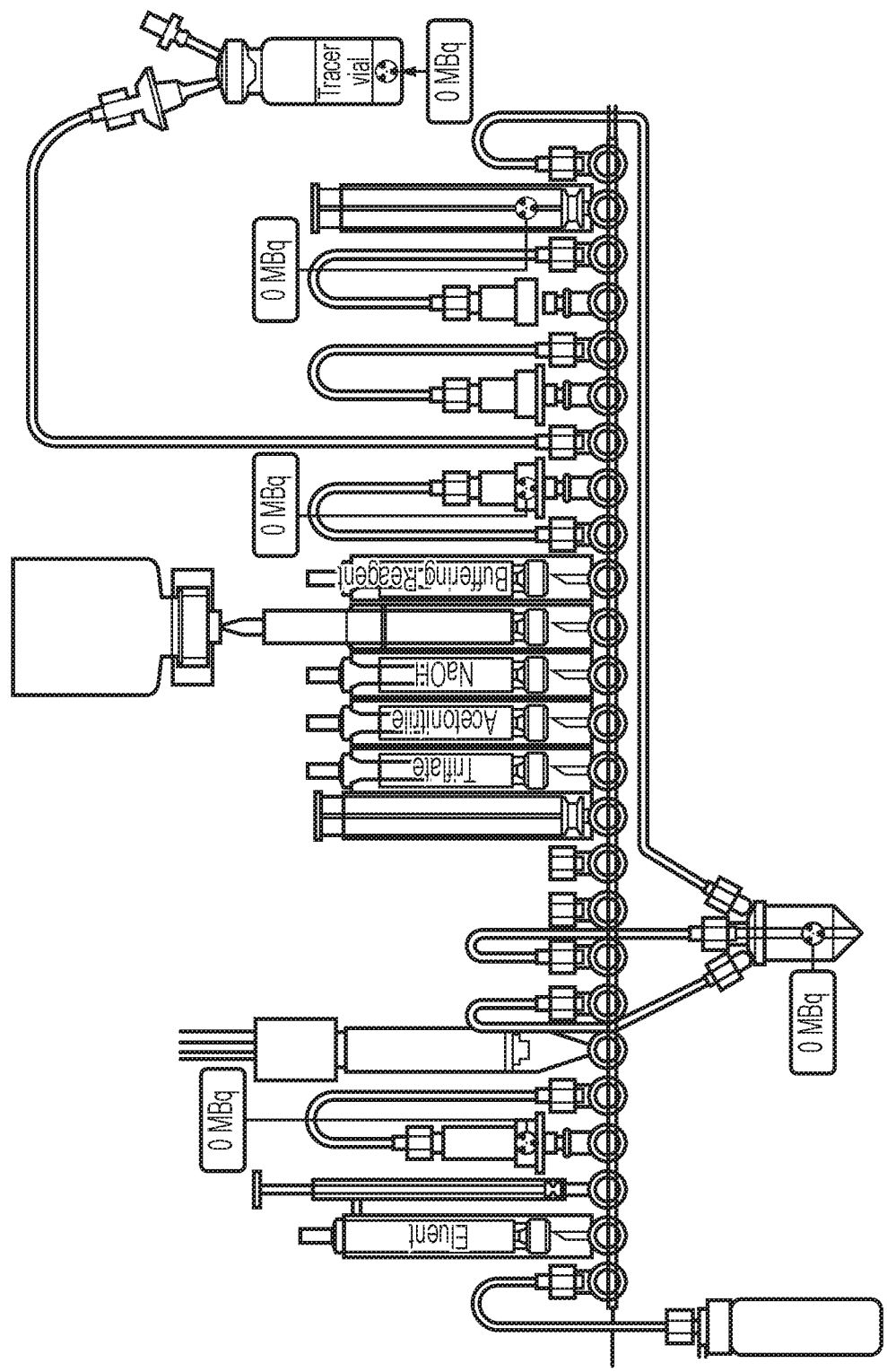
FIG. 1 and FIG. 2 illustrate examples of known cassettes for the production of one batch per cassette of an $^{18}$F-labelled compound.

To more clearly and concisely describe and point out the subject matter of the claimed invention, definitions are provided hereinbelow for specific terms used throughout the present specification and claims. Any exemplification of specific terms herein should be considered as a non-limiting example.

The term "purifying" as used herein may be taken to mean a process to obtain substantially pure $^{18}$F-labelled compound. The term "substantially" refers to the complete or nearly complete extent or degree of an action, characteristic, property, state, structure, item, or result. The term "substantially pure" can be taken to mean completely pure $^{18}$F-labelled compound, which would be ideal, but also $^{18}$F-labelled compound that is sufficiently pure to be suitable for use as a PET tracer. The term "suitable for use as a PET tracer" means that the substantially pure $^{18}$F-labelled compound is suitable for intravenous administration to a mammalian subject followed by PET imaging to obtain one or more clinically-useful images of the location and/or distribution of the $^{18}$F-labelled compound.

An "$^{18}$F-labelled compound" is a chemical compound that comprises an $^{18}$F atom. Non-limiting examples of $^{18}$F-labelled compounds include [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F]fluorocyclobutane-1-carboxylic acid ([$^{18}$F]FACBC), [$^{18}$F]-flumanezil ([$^{18}$F]FMZ), [$^{18}$F]-tyrosine, [$^{18}$F]-altanaserine, 4-[$^{18}$F]-fluoro-3-iodobenzyl guanidine ([$^{18}$F]-FIBG), meta-[$^{18}$F]fluorobenzylguanidine ([$^{18}$F]-mFBG) and [$^{18}$F]-5-fluorouracil.

In one embodiment of the present invention the $^{18}$F-labelled compound is selected from [$^{18}$F]FDG, [$^{18}$F]FMISO, [$^{18}$F]FLT and [$^{18}$F]FACBC. In another embodiment of the present invention the $^{18}$F-labelled compound is [$^{18}$F]FDG.

In the context of the present invention the terms "first batch" and "second batch" represent two separate consecutive syntheses of $^{18}$F-labelled compound produced on the same cassette, the second batch being produced only after production of the first batch has been completed, i.e. the product has been collected in the product collection vial. The term "batch" is used to refer variously to the final $^{18}$F-labelled product and to the reaction mixture prior to obtaining the final $^{18}$F-labelled product. It is intended that the two batches can be produced on the same day and without need to open the hot cell in which the cassette and automated synthesiser are present.

By the term "cassette" is meant a piece of apparatus designed to fit removably and interchangeably onto an automated synthesis apparatus, in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. In one embodiment each valve is a 3-way valve. In one embodiment each valve is a stopcock valve comprising a rotatable stopcock. Each valve has a male-female joint which interfaces with a corresponding moving arm of the automated synthesis apparatus. External rotation of the arm thus controls the opening or closing of the valve when the cassette is attached to the automated synthesis apparatus. Additional moving parts of the automated synthesis apparatus are designed to clip onto syringe plunger tips, and thus raise or depress syringe barrels. The cassette is versatile, typically having several positions where reagents can be attached, and several suitable for attachment of syringe vials of reagents or chromatography columns. The cassette always comprises a reaction vessel, generally configured such that 3 or more ports of the cassette are connected thereto to permit transfer of reagents or solvents from various ports on the cassette. Cassettes need to be designed to be suitable for radiopharmaceutical manufacture and are therefore manufactured from materials which are of pharmaceutical grade as well as resistant to radiolysis. In one embodiment of the present invention the single-use cassette is a FASTlab™ cassette, i.e. one which is suitable for use with a FASTlab™ automated synthesis apparatus.

The term "single-use" as used in the context of a cassette of the present invention means that the cassette is intended to be used once prior to disposal for the production of two batches of an $^{18}$F-labelled compound.

By the term "automated synthesis apparatus" is meant an automated module based on the principle of unit operations as described by Satyamurthy et al (1999 Clin Positr Imag; 2(5): 233-253). The term 'unit operations" means that complex processes are reduced to a series of simple operations or reactions, which can be applied to a range of materials. Such automated synthesis apparatuses are preferred for the method of the present invention especially when a radiopharmaceutical composition is desired. They are commercially available from a range of suppliers (Satyamurthy et al, above), including: GE Healthcare; CTI Inc; Ion Beam Applications S. A. (Chemin du Cyclotron 3, B-1348 Louvain-La-Neuve, Belgium); Raytest (Germany) and Bioscan (USA). Automated synthesis apparatuses are designed to be employed in a suitably configured radioactive work cell, or "hot cell", which provides suitable radiation shielding to protect the operator from potential radiation dose, as well as ventilation to remove chemical and/or radioactive vapours. Using a cassette the automated synthesis apparatus has the flexibility to make a variety of different radiopharmaceuticals with minimal risk of cross-contamination, by simply changing the cassette. This approach also has the advantages of simplified set-up hence reduced risk of operator error, improved GMP (good manufacturing practice) compliance, multi-tracer capability, rapid change between production runs, pre-run automated diagnostic checking of the cassette and reagents, automated barcode cross-check of chemical reagents vs the synthesis to be carried out, reagent traceability, single-use and hence no risk of cross-contamination, tamper and abuse resistance.

The "reaction mixture comprising an $^{18}$F-labelled compound" referred to in the system of the present invention is the solution obtained directly following labelling of a precursor compound with $^{18}$F, i.e. before removal of any protecting groups and before any purification steps.

The term "labelling" used in connection with labelling a precursor compound with $^{18}$F such that $^{18}$F becomes covalently bound to said precursor compound. Said labelling is often carried out by adding reactive [$^{18}$F]fluoride to a solution of the precursor compound in a reaction vessel and elevating the temperature, e.g. to around 100-150° C. for a short duration of around 2-10 minutes.

A "precursor compound" is to be understood herein as a non-radioactive derivative of a radiolabelled compound, designed so that chemical reaction with a convenient chemical form of the detectable label occurs site-specifically in the minimum number of steps (ideally a single step) to give the desired radiolabelled compound. Such precursor compounds are synthetic and can conveniently be obtained in good chemical purity. A number of precursor compounds are well known to be suitable for the synthesis of $^{18}$F-labelled compounds, as taught for example in Chapter 7 of "Handbook of Radiopharmaceuticals: Radiochemistry and Applications" (2003 John Wiley & Sons Ltd., Wench & Redvanly, Eds.).

The term "protecting group" refers to a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007).

The term "solid phase extraction (SPE)" refers to a sample preparation process by which compounds in a solution are separated from each other based on their respective affinities for a solid (the "solid phase", or "stationary phase") through which the sample is passed and the solvent (the "mobile phase" or "liquid phase") in which they are dissolved. The result is that a compound of interest is either retained on the solid phase or in the mobile phase. The portion that passes through the solid phase is collected or discarded, depending on whether it contains the compound of interest. If the portion retained on the stationary phase includes the compound of interest, it can then be removed from the stationary phase for collection in an additional step, in which the stationary phase is rinsed with another solution known as an "eluent". For the present invention SPE is suitably carried out using an "SPE column" (also often referred to as an "SPE cartridge"), which is readily available commercially and is typically in the form of a syringe-shaped column packed with solid phase. Most known solid phases are based on silica that has been bonded to a specific functional group, e.g. hydrocarbon chains of variable length (suitable for reversed-phase SPE), quaternary ammonium or amino groups (suitable for anion exchange), and sulfonic acid or carboxyl groups (suitable for cation exchange).

"Reversed-phase SPE" makes use of a nonpolar modified solid phase and a polar mobile phase. Compounds are retained by hydrophobic interactions and eluted using a non-polar elution solvent to disrupt the forces that bind the compound to the solid phase. Non-limiting examples of reversed-phase SPE columns include those wherein the chemistry is selected from octadecyl (C18 or tC18), octyl (C8), cyano (CN), diol, hydrophilic modified styrene polymer (HLB e.g. Oasis® HLB from Waters), polymeric poly(divinylbenzene-vinylpyrrolidone) (e.g. Porapak® RDX resin available from Waters), and $NH_2$ SPE columns. The term "chemistry" in the context of SPE columns refers to the surface groups that interact with the solution being purified and typically an SPE column is referred to by its chemistry, e.g. a SPE column with C18 chemistry is referred to as a "C18 column" In one embodiment of the present invention the chemistry of the reversed-phase SPE column is a tC18 column or a HLB column. In another embodiment of the present invention the reversed-phase SPE column is a tC18 column. In some embodiments of the present invention the tC18 column is an environmental tC18 column, sometimes referred to as a long tC18 column or a tC18 plus column.

"Normal-phase SPE" makes use of a polar modified solid phase and a non-polar mobile phase. Compounds are retained by hydrophilic interactions and eluted using a solvent that is more polar than the original mobile phase to disrupt the binding mechanism. Non-limiting examples of normal-phase SPE columns include alumina, diol and silica SPE columns.

"Anion exchange SPE" utilises electrostatic attraction of charged group on compound to a charged group on the sorbent's surface and can be used for compounds that are charged in solution. The primary retention mechanism of the compound is based mainly on the electrostatic attraction of the charged functional group on the compound to the charged group that is bonded to the silica surface. A solution having a pH that neutralizes either the compound's functional group or the functional group on the sorbent surface is used to elute the compound of interest. A non-limiting example of an anion exchange SPE column is a quaternary ammonium anion exchange (QMA) SPE column.

The term "eluent" used hereinabove in connection with SPE generally is also specifically used in connection with the single-use cassette of the present invention to refer to the eluent used to elute $^{18}$F-fluoride trapped on the anion exchange column. $^{18}$F-fluoride suitable for use in the synthesis of an $^{18}$F-labelled compound is normally obtained as an aqueous solution from the nuclear reaction $^{18}$O (p,n)$^{18}$F. In order to increase the reactivity of $^{18}$F-fluoride and to reduce or minimise hydroxylated by-products resulting from the presence of water, water is typically removed from $^{18}$F-fluoride prior to the reaction, and fluorination reactions are carried out using anhydrous reaction solvents (Aigbirhio et al 1995 J Fluor Chem; 70: 279-87). A further step that is used to improve the reactivity of $^{18}$F-fluoride for radiofluorination reactions is to add a cationic counterion prior to the removal of water. This cationic counterion is dissolved in an organic-aqueous solution and this solution is used as an eluent for eluting $^{18}$F-fluoride from an anion exchange column on which the $^{18}$F-fluoride has been trapped. Suitably, the counterion should possess sufficient solubility within the anhydrous reaction solvent to maintain the solubility of the $^{18}$F-fluoride. Therefore, counterions that are typically used include large but soft metal ions such as rubidium or caesium, potassium complexed with a cryptand such as Kryptofix™ 222, or tetraalkylammonium salts, wherein potassium complexed with a cryptand such as Kryptofix™ 222, or tetraalkylammonium salts are preferred. The term Kryptofix™ 222 (or K222) refers herein to a commercially-available preparation of the compound 4,7,13,16,21,24-Hexaoxa-1,10-diazabicyclo[8.8.8]hexacosane.

An "SPE column for deprotection" in the context of the present invention is an SPE column having a solid phase on which a precursor compound having protecting groups is retained following the $^{18}$F-labelling reaction in order to remove the protecting groups and obtain the desired $^{18}$F-labelled compound. In one embodiment the SPE column for deprotection is a reversed-phase SPE column as defined herein.

The terms "first end" and "second end" are used in the context of the two ends of an SPE column. In certain embodiments, the first end is proximal to the common pathway and the second end is distal to the common pathway.

The term "selectively fluidly connected" used in connection with a feature of the present invention means that it is possible to select whether or not fluid can pass to and/or from the feature to another feature of the invention, e.g. by use of a suitable valve. In one embodiment of the invention a suitable valve is a 3-way valve having three ports and means to put any two of the three associated ports in fluid communication with each other while fluidly isolating the third port. In another embodiment of the invention a suitable valve is a stopcock valve comprising a rotatable stopcock.

The term "common pathway" is to be understood to be a fluid pathway to which the other components of the system or of single-use cassette of the present invention are selectively fluidly connected. In one embodiment, the common pathway is a linear fluid pathway. In one embodiment, the common pathway is made from a rigid pharmaceutical grade polymeric material that is resistant to radiation. Non-limiting examples of suitable such materials include polypropylene, polyethylene, polysulfone and Ultem®. In one embodiment, said common pathway is made from polypropylene or polyethylene.

The "product collection vial" is suitably a clinical grade syringe or a container which is provided with a seal which is suitable for single or multiple puncturing with a hypodermic needle (e.g. a crimped-on septum seal closure) whilst maintaining sterile integrity. Suitable containers comprise a sealed vessel which permits maintenance of sterile integrity and/or radioactive safety, whilst permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired e.g. to change the headspace gas or degas solutions.

A "reaction vessel" in the context of the present invention is a container selectively fluidly connected to the common pathway of the single-use cassette of the invention in order that the reactants and reagents required for the synthesis can be sent to the reaction vessel and the product(s) removed in an appropriate order. The reaction vessel has an internal volume suitable for containing the reactants and reagents and is made from pharmaceutical grade materials resistant to radiation.

The term "means for cleaning" refers to a source of reagent selectively fluidly connected to the component to be cleaned. The selective fluid connection suitably comprises a valve and length of flexible tubing. Suitable reagents for cleaning include ethanol and acetonitrile, aqueous solutions thereof, and water. The term "cleaning" in the context of the present invention refers to the process of passing a suitable amount of one or more reagents through a component to be cleaned in order to render it suitable for use in preparation of the second batch of $^{18}$F-labelled compound.

The term "reagent vial" is taken to mean a vial containing one of the reagents for use in the production of the $^{18}$F-labelled compound. A typical reagent vial is made from a rigid pharmaceutical grade polymer resistant to radiation. Suitable reagents contained in said reagent vials include ethanol, acetonitrile, deprotecting agent and buffer. In one embodiment said deprotecting agent is selected from HCl, NaOH and $H_3PO_4$. In one embodiment said deprotecting agent is NaOH. In one embodiment said buffer is based on a weak acid, for example selected from citrate, phosphate, acetate and ascorbate. For example where the $^{18}$F-labelled compound of the present invention is [$^{18}$F]FDG, the single-use cassette comprises a reagent vial containing ethanol, one containing acetonitrile, another containing NaOH and another containing a buffer based on a weak acid selected from citrate or phosphate.

The term "sufficient" as used in the context of eluent and precursor compound for the two consecutive batches means a suitable amount thereof to ensure that two batches of the $^{18}$F-labelled compound can be obtained. Generally this amount is a little more than the exact amount required.

The term "passing" refers to the act of allowing a reactant, reagent or reaction solution to flow through a particular component by the selective opening of valves.

The term "eluting" refers to passing a solution through an SPE column with the aim to release a compound or compounds of interest that has or have been bound to the solid phase.

The term "partially purified" refers to where in the reaction solution comprising the $^{18}$F-labelled compound of interest has been subjected to a purification step but is not yet substantially pure, where the term "substantially pure is defined hereinabove.

In one embodiment of the method of the present invention the steps are carried out in sequence.

In one embodiment of steps (v) and (xi) of the method of the present invention said passing in each case is directly from said normal-phase SPE column to said product collection vial.

Figure 4:
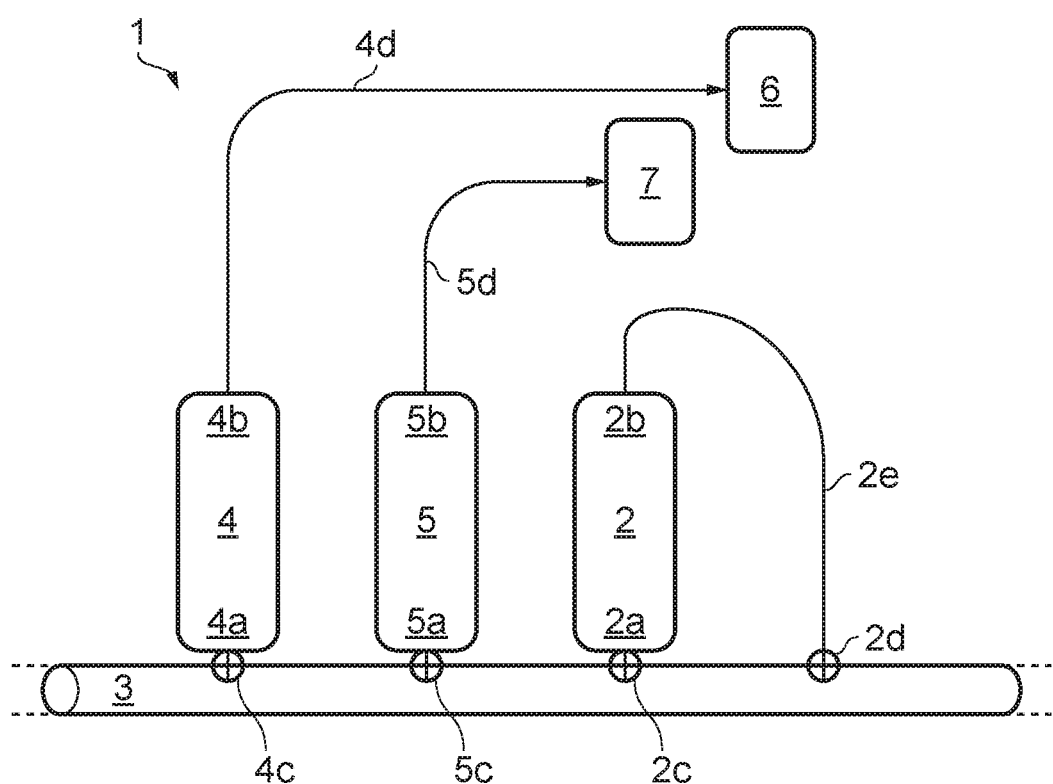
FIG. 4 illustrates an exemplary system of the present invention for purifying two consecutive batches per cassette of a reaction mixture comprising an $^{18}$F-labelled compound.
Figure 5:
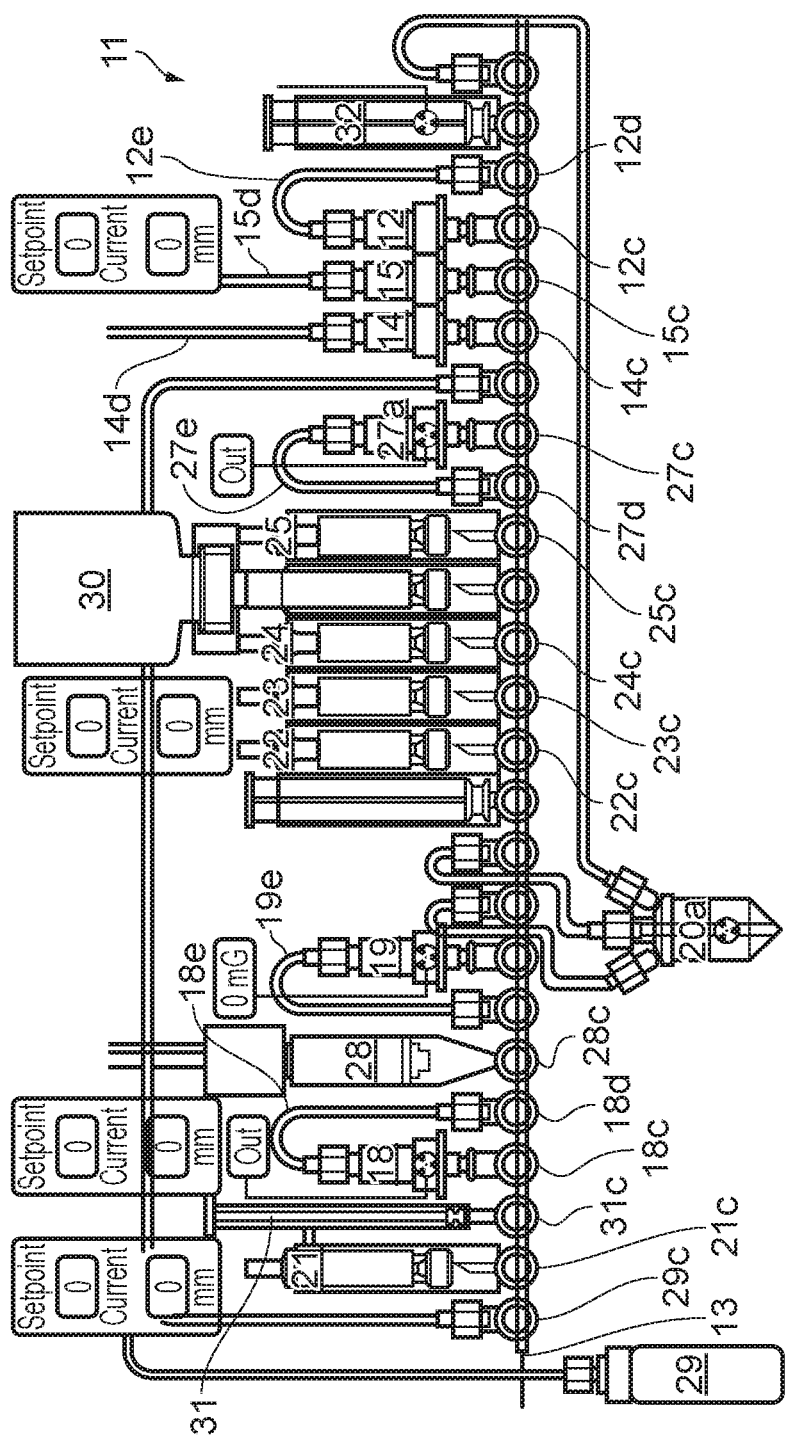
FIG. 5 illustrates an exemplary single-use cassette of the present invention for preparing two consecutive batches per cassette of an [$^{18}$F]-labelled compound.

Non-limiting examples of embodiments of the present invention are illustrated in FIGS. 4 and 5.

FIG. 4 illustrates an exemplary system of the present invention and shows a reversed-phase SPE column (2) with a first end (2a) proximal to a common pathway (3) and a second end (2b) distal to the common pathway (3). The first end (2a) of the reversed-phase SPE column (2) is selectively fluidly connected to the common pathway (3) by means of a valve (2c). The second end (2b) of the reversed-phase SPE column (2) is selectively fluidly connected to the common pathway (3) by means of a valve (2d) and a length of flexible tubing (2e). Also illustrated are first (4) and second (5) normal-phase SPE columns, each having respective first (4a, 5a) and second (4b, 5b) ends. The respective first ends (4a, 5a) of the first (4) and second (50 normal-phase SPE columns are selectively fluidly connected to the common pathway (3) by means of respective valves (4c, 5c). The respective second ends (4b, 5b) of the first (4) and second (50 normal-phase SPE columns are fluidly connected to respective product collection vials (6, 7) by means of respective lengths of flexible tubing (4d, 5d).

FIG. 5 illustrates an exemplary single-use cassette of the present invention, suitable for the production of two sequential batches of [$^{18}$F]-FDG. All components are selectively fluidly connected to a common pathway 13 by means of a linear series of identical 3-way valves (e.g. 12c, 12d, 14c, 15c, 18c, 18d, 21c, 22c, 23c, 24c, 25c, 27c, 28c, 29c, 31c). Each valve is a stopcock valve comprising a rotatable stopcock. Each valve is linked to a port where a component is attached and has a male-female joint which interfaces with a corresponding moving arm of the automated synthesis apparatus which controls the opening or closing of the valve when the cassette is attached to the apparatus.

Production of a first batch of [$^{18}$F]-FDG using the cassette of FIG. 5 is initiated when [$^{18}$F]-fluoride produced by a $^{18}$O (p,n)$^{18}$F$^-$ reaction enters the cassette via vial 28 and travels along common pathway 13 to QMA 18 via valves 28c and 18d and tubing 18e. The $^{18}$R is retained by an ion-exchange reaction and $^{18}$O-water is allowed to flow through the common pathway 13 of the cassette via valves 18c and 29c to be recovered in vial 29. $^{18}$F-fluoride retained on QMA 18 is then eluted with eluent (acetonitrile solution of Kryptofix™ 222 and potassium carbonate) from vial 21 withdrawn in syringe 31 and into the reaction vessel 20a. Water is evaporated and mannose triflate precursor 22 is added to the reaction vessel 20a. The $^{18}$F-labelled mannose triflate ($^{18}$F-fluoro-tetraacetyl-glucose, FTAG) is trapped and so separated from $^{18}$F fluorides on an environmental tC18 SPE 27*a* via tubing 27*e* to undergo hydrolysis with NaOH 24 to remove acetyl protecting groups. The resulting hydrolyzed basic solution is then neutralized in the syringe 32 with buffer 25. Removal of weakly hydrophilic impurities takes place on tC18 SPE column 12 via tubing 12*e*. Residual $^{18}$F fluoride removal takes place on a first alumina SPE 14 and the final purified solution of $^{18}$F-FDG is transferred to a collection vial via tubing 14*d*.

Cleaning of the tC18 environmental 27*a* and the tC18 12 is carried out with ethanol (from vial 23) and water (from water bag 30) before starting production of a second batch of [$^{18}$F]-FDG. The second batch production proceeds via the same steps as above described for the first batch, except that QMA SPE 19 and alumina SPE 15 are used.

Any commonly-present features and embodiments of the present invention are equally applicable across the various aspects of the present invention.

BRIEF DESCRIPTION OF THE EXAMPLES

Example 1 describes how two consecutive batches of [$^{18}$F]FDG in citrate buffer were produced on the FASTlab™ using one FASTlab™ cassette.

Example 2 describes analysis of extractables from alumina column used in the production of two consecutive batches of [$^{18}$F]FDG on one FASTlab™ cassette.

List of Abbreviations Used in the Examples

EtOH ethanol
[$^{18}$F]FDG $^{18}$F-fluorodeoxyglucose
[$^{18}$F]FDGc citrate-buffered $^{18}$F-fluorodeoxyglucose
[$^{18}$F]FTAG $^{18}$F-fluoro-tetraacetyl-glucose
IC ionic chromatography
ICP-MS inductively coupled plasma mass spectrometry
K222 4,7,13,16,21,24-Hexaoxa-1,10-diazabicyclo[8.8.8]hexacosane
KI potassium iodide
LB low bleed phase
mCi milli Curie
MeCN acetonitrile
ppm parts per million
QMA quaternary methylammonium
TLC thin layer chromatography

EXAMPLES

Example 1: Dual Run [$^{18}$F]FDG Citrate on the FASTlab™

Two batches of [$^{18}$F]FDG were synthesised using the FASTlab™ cassette illustrated in FIG. 5 using the following steps:
(1) The tC18 environmental and tC18 plus columns were each conditioned with ethanol (from position 13) and water (from position 15).
(2) [$^{18}$F]-fluoride was obtained from the bombardment of [$^{18}$O]—H$_2$O with a high-energy proton beam extracted from a Cyclone Cyclotron 18/9 (IBA) and transferred to the FASTlab™ cassette in the conical reservoir.
(3) [$^{18}$F]Fluoride was trapped on the QMA column at position 4 and separated from the enriched water which was collected in an external vial via a pathway through positions 5-4-1.
(4) Eluent was withdrawn in the syringe at position 3 and passed through the QMA column to release [$^{18}$F]fluoride and send to the reaction vessel.
(5) Evaporation of water in the reaction vessel was catalysed by adding a little quantity of mannose triflate precursor (25 mg/mL; vial at position 12) at 120° C.
(6) Mannose triflate precursor was withdrawn in the syringe at position 11 and transferred to the reaction vessel (connected via tubing to positions 9, 10 and 25) for the labelling reaction to take place at 125° C. for 2 minutes.
(7) The resulting radiolabelling compound ($^{18}$F-fluoro-tetraacetyl-glucose, [$^{18}$F]FTAG) was trapped and so, separated from unreacted fluorides, on the upper side of the tC18 environmental column at position 18.
(8) Sodium hydroxide was passed through the column to convert the [$^{18}$F]FTAG to [$^{18}$F]FDG collected by the syringe at position 24.
(9) Neutralization of the resulting basic solution was carried out using hydrochloric acid contained in a citrate buffer.
(10) The product was purified first through the tC18 plus column (at position 22) and then through the Alumina A (at position 20) and then directly to the first product collection vial.
(11) The tC18 environmental was rinsed with 1 mL of ethanol and 4 mL of water, the tC18 plus was rinsed with 1 mL of ethanol and 2 mL of water.
(12) A second batch of [$^{18}$F]-fluoride from the cyclotron was transferred to the FASTlab™ cassette as in step (2).
(13) The [$^{18}$F]fluoride was trapped on a new QMA column found at position 8 and separated from the enriched water which is collected in an external vial via a pathway through positions 7-8-19-1.
(14) With [$^{18}$F]fluoride from the QMA at position at, steps (4)-(9) were carried out as for the first batch.
(15) The final [$^{18}$F]FDG for the second batch was purified with the pathway: tC18 plus column (at position 22)—Alumina A found at position 21 directly connected to the second product collection vial.

Starting activity, final activity and residual activities were measured by a calibrated ionization chamber VEENSTRA (VIK-202).

To determine yield, the following yield calculations were made:
if delta Tf=elapsed time after time at starting of the synthesis in min
if Af=final activity in mCi
cAf=corrected final activity in mCi regarding to starting of the synthesis in min=Af. Exp(ln(2)*(delta Tf/110))
where 110=half-life of [$^{18}$F]fluorine in minutes
if cAi=corrected starting activity in mCi regarding to starting of the synthesis in mCi
if delta Ts=duration of the synthesis Corrected yield (CY)=(cAf/cAi)*100

Uncorrected yield (NCY)=CY*Exp(ln(2)*(−delta Ts/110))

The amount of Kryptofix™ 222 in the final product was determined by spotting the sample on a TLC plate which is impregnated by a revealing solution of iodoplatinate (0.5 g of Chloroplatinic acid hexa-hydrated: H$_2$PtCl$_6$.6H$_2$O (!highly hygroscopic!), 9 g of potassium iodide: KI, 200 mL of distilled water) and comparing this with standard solutions of Kryptofix™ 222 1, 5, 10, 50 and 100 ppm). Colour intensity of the obtained stains is proportional to the amount of Kryptofix™ 222 present in the solution.

The amount of ethanol in the final product was determined by injecting the sample into a chromatography system called gas chromatography (VARIAN CP-3800, including auto-sampler, column inlet, column oven and flame ionization detector).

The GC column was a Macherey-Nagel OPTIMA 624 (6% cyanopropylphenyl—94% dimethylpolysiloxane), LB (=Low Bleed phase), 30 m (=length), 0.32 mm (=inner diameter), 1.8 µm (=film thickness).

The following parameters were used:
Mobile phase=helium (flow=5 mL/min)
Injection samples (injection volume=0.5 µL)
1. 1.6 mL water (=blank)
2. 1.6 mL standard solution (5000 ppm in EtOH; 273 ppm in MeCN)
3. 1.6 mL sample requiring analyses
Gas flow to detector: —helium (=20 mL/min)
hydrogen (=35 mL/min)
compressed air (=360 mL/min)
Injector temperature=200° C.
Column oven temperature=temperature ramp from 50° C. to 220° C.
Detector temperature=250° C.
Acquisition time=15 minutes The results below are obtained with this cassette configuration (Runs 1a and 1b from one cassette and Runs 2a and 2b from another cassette):

| Run | Starting activity (in mCi) | Yield (non-corrected; %) | Residual activity on QMA (%) | Residual activity in enriched water vial (%) | K222 in the final product (ppm) | EtOH in the final product (ppm) |
|---|---|---|---|---|---|---|
| 1a | 8.403 | 67.72 | 0.11 | — | 1 | 1329 |
| 1b | 7.970 | 31.21 | 0.85 | — | 1 | 2495 |
| 2a | 9.050 | 66.56 | 0.14 | 0.04 | 1 | 1987 |
| 2b | 9.116 | 29.45 | 0.71 | 0.04 | 1 | 4258 |

Example 2: Analysis of Extractables from Alumina Column

Figure 2:
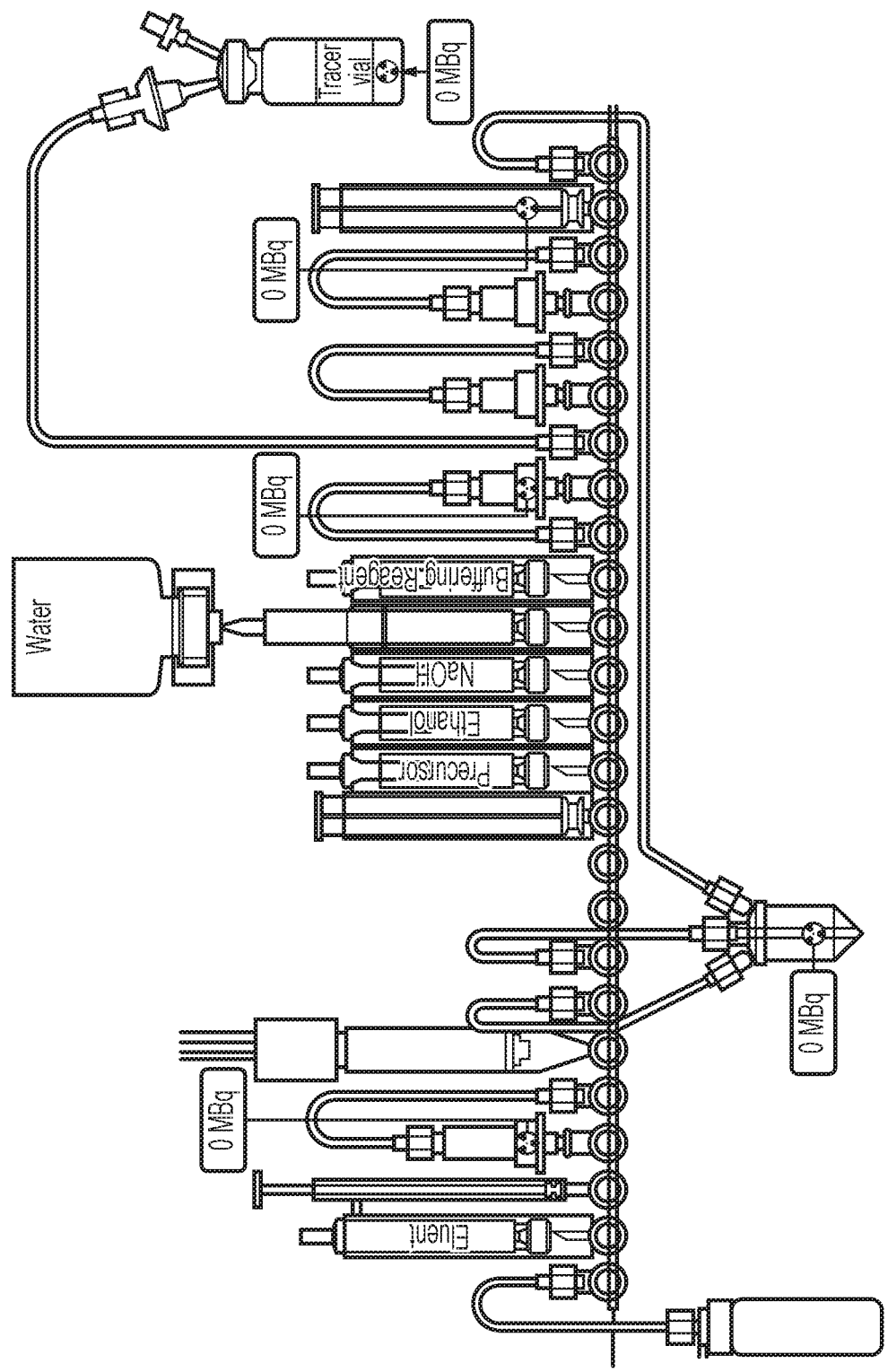
Figure 3:
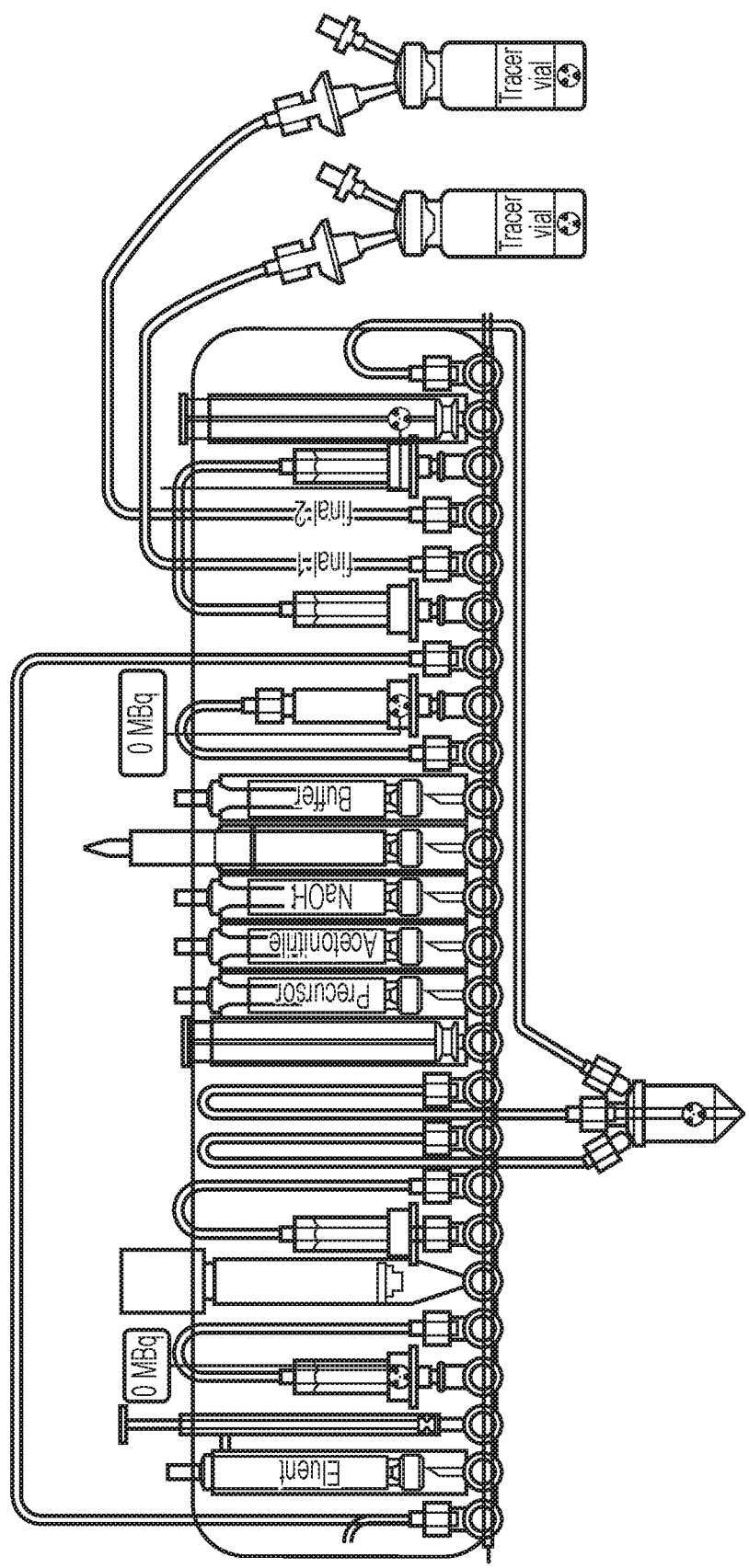
FIG. 3 illustrates an exemplary cassette described in WO2015071288.

A comparative study was done between samples coming from the known citrate-buffered [$^{18}$F]FDG synthesis using the FASTlab cassette illustrated in FIG. 2 (alumina column washed with water before use) and samples from the synthesis according to an exemplary system of the present invention (FIG. 5, alumina columns not washed with water before use).

The concentration of the chemical elements was analysed by ICP-MS (Inductively Coupled Plasma Mass Spectrometry) and cold impurities were analysed by IC (ionic chromatography).

ICP-MS analyses were performed on 5×2 batches of samples obtained using the exemplary method of the invention (cassette of FIG. 5). The results are presented in the table below:

| Sample ID | Al (ppm) | Si (ppm) |
|---|---|---|
| 3a | 5.8 | 2.0 |
| 3b | 10.0 | 2.5 |
| 4a | 6.0 | 2.3 |
| 4b | 10.0 | 2.9 |
| 5a | 6.6 | 2.5 |
| 5b | 10.0 | 3.0 |
| 6a | 10.0 | 1.3 |
| 6b | 23.0 | 4.0 |
| 7a | 13.0 | 1.3 |
| 7b | 18.0 | 2.1 |
| MEAN (ppm) | 11.2 | 2.4 |

The table below shows the ICP-MS data resulting from analysis of three samples obtained using the prior art process (i.e. where the alumina column is rinsed with water during the synthesis process; cassette of FIG. 2):

| Sample ID (Oslo) | Al (ppm) | Si (ppm) |
|---|---|---|
| 8 | 30 | 19 |
| 9 | 29 | 15 |
| 10 | 24 | 17 |
| MEAN (ppm) | 27.7 | 17 |

The invention claimed is:

1. A single-use cassette for preparing two consecutive batches of an [$^{18}$F]-labelled compound, said cassette comprises:
   (a) a reversed-phase SPE column having a first end and a second end, wherein each of said first end and said second end is selectively fluidly connected to a linear common pathway, and means for cleaning said SPE column; and,
   (b) first and second normal-phase SPE columns, each having a first end selectively fluidly connected to said linear common pathway and a second end fluidly connected to a product collection vial;
   (c) two anion exchange SPE columns;
   (d) a reaction vessel and means for cleaning said reaction vessel;
   (e) a eluent vial containing sufficient eluent for said two consecutive batches;
   (f) a precursor vial containing sufficient precursor compound for said two consecutive batches;
   (g) reagent vials each containing a particular reagent in sufficient quantity for said two consecutive batches; and
   (h) a deprotection SPE column for deprotection and means for cleaning said SPE column,
wherein the reversed-phase SPE column, first normal-phase SPE column, second normal-phase SPE column, two anion exchange SPE columns, reaction vessel, eluent vial, precursor vial, reagent vials and deprotection SPE column are connected to the linear common pathway within the cassette.

2. The cassette of claim 1, wherein the chemistry of said reversed-phase SPE column is selected from octadecyl (C18 or tC18), octyl (C8), cyano (CN), diol, hydrophilic modified styrene polymer (HLB), polymeric poly(divinylbenzene-vinylpyrrolidone), and NH$_2$.

3. The cassette of claim 1, wherein said reversed-phase SPE column is selected from a tC18 and a HLB SPE column.

4. The cassette of claim 1, wherein said reversed-phase SPE column is a tC18 column.

5. The cassette of claim 1, wherein each of said first and second normal-phase SPE columns is an alumina SPE column.

6. The cassette of claim 1, wherein each of said anion exchange SPE columns is a quaternary ammonium anion exchange (QMA) column.

7. The cassette of claim 1, wherein each of said means for cleaning comprises a source of sterile water and/or a source of an organic solvent selectively fluidly connected respectively to said reversed-phase SPE column, said reaction vessel, and said SPE column for deprotection.

8. The cassette of claim 1, wherein said eluent comprises a cationic counterion dissolved in an organic-aqueous solution.

9. The cassette of claim 1, wherein said reagent vials comprise a vial containing ethanol, a vial containing acetonitrile, a vial containing a deprotecting agent, and a vial containing buffer.

10. A method for purifying a first batch and a second batch of a reaction mixture comprising an $^{18}$F-labelled compound in a cassette, said method comprises:
   (I) passing said first batch of said reaction mixture through a reversed-phase SPE column;
   (II) eluting said reversed-phase SPE column to obtain a partially purified first batch of said reaction mixture;
   (III) passing said partially purified first batch of said reaction mixture through a first normal-phase SPE column;
   (IV) eluting said first normal-phase SPE column to obtain a purified first batch of said reaction mixture;
   (V) passing said purified first batch of said reaction mixture into a product collection vial;
   (VI) cleaning said reversed-phase SPE column; and, (VII) passing said second batch of said reaction mixture through said cleaned reversed-phase SPE column;
   (VIII) eluting said reversed-phase SPE column to obtain a partially purified second batch of said reaction mixture;
   (IX) passing said partially purified second batch of said reaction mixture through a second normal-phase SPE column (X) eluting said second normal-phase SPE column to obtain a purified second batch of said reaction mixture; and
   (XI) passing said purified second batch of said reaction mixture into a product collection vial,
   wherein the reversed-phase SPE column, first normal-phase SPE column, and product collection vial are connected to the linear common pathway within the cassette.

11. The method of claim 10, wherein steps (I)-(XI) are carried out in sequence.

12. The method of claim 10, wherein said $^{18}$F-labelled compound is selected from [$^{18}$F]FDG, [$^{18}$F]FMISO, [$^{18}$F]FLT, and [$^{18}$F]FACBC.

13. A method for the production of a first batch and a second batch of an $^{18}$F-labelled compound wherein said method comprises:
   (A) labelling a first aliquot of a precursor compound with $^{18}$F-fluoride;
   (B) deprotecting the $^{18}$F-labelled product of step (A) on a reversed-phase SPE column;
   (C) carrying out steps I-VI as defined in claim 10 on the reaction mixture comprising an $^{18}$F-labelled compound obtained from steps (A) and (B);
   (D) cleaning the reversed-phase SPE column(s);
   (E) labelling a second aliquot of a precursor compound with $^{18}$F-fluoride;
   (F) deprotecting the $^{18}$F-labelled product of step (D) on a reversed-phase SPE column; and
   (G) carrying out steps VII-XI as defined in claim 10 on the reaction mixture comprising an $^{18}$F-labelled compound obtained from steps (E) and (F).

14. The method of claim 13, wherein said $^{18}$F-labelled compound is selected from [$^{18}$F]fluorodeoxyglucose ([$^{18}$F]FDG), [$^{18}$F]Fluoromisonidazole ([$^{18}$F]FMISO), [$^{18}$F]fluorothymidine ([$^{18}$F]FLT), [$^{18}$F]Fluoroazomycin arabinofuranoside ([$^{18}$F]FAZA), [$^{18}$F]Fluoroethyl-choline ([$^{18}$F]FECH), [$^{18}$F]fluorocyclobutane-1-carboxylic acid ([$^{18}$F]FACBC), [$^{18}$F]-flumanezil ([$^{18}$F]FMZ), [$^{18}$F]-tyrosine, [$^{18}$F]-altanaserine, 4-[$^{18}$F]-fluoro-3-iodobenzyl guanidine ([$^{18}$F]-FIBG), meta-[$^{18}$F]fluorobenzylguanidine ([$^{18}$F]-mFBG), and [$^{18}$F]-5-fluorouracil.

15. The method of claim 13, wherein said $^{18}$F-labelled compound is selected from [$^{18}$F]FDG, [$^{18}$F]FMISO, [$^{18}$F]FLT, and [18F]FACBC.

* * * * *